United States Patent [19]

Mandanis

[11] Patent Number: 5,485,887
[45] Date of Patent: Jan. 23, 1996

[54] PNEUMATIC IMPACT TOOL AND PISTON FOR A PNEUMATIC IMPACT TOOL

[75] Inventor: Georges Mandanis, Luzern, Switzerland

[73] Assignee: IMT Integral Medizintechnik AG, Ennetburgen, Switzerland

[21] Appl. No.: 216,059

[22] Filed: Mar. 22, 1994

[30] Foreign Application Priority Data

Mar. 30, 1993 [CH] Switzerland ................. 976/93

[51] Int. Cl.$^6$ ............. B25D 17/06; B25D 17/24
[52] U.S. Cl. ............. 173/17; 173/91; 173/135; 173/211; 173/169
[58] Field of Search ............. 173/17, 91, 136, 173/135, 169, 211

[56] References Cited

U.S. PATENT DOCUMENTS

| | | |
|---|---|---|
| 1,014,295 | 1/1912 | Gibb et al. . |
| 1,264,318 | 4/1918 | McGrath . |
| 1,440,731 | 1/1923 | Gartin . |
| 2,426,409 | 8/1947 | O'Farrell ............. 121/18 |
| 2,440,457 | 4/1948 | Beckwith ............. 121/32 |
| 2,655,921 | 10/1953 | Haboush ............. 128/305 |
| 3,456,739 | 7/1969 | Sagae ............. 173/91 |
| 3,583,499 | 6/1971 | Cordes ............. 173/131 |
| 3,891,036 | 6/1975 | Schmidt ............. 173/91 |
| 4,114,950 | 9/1978 | Cooper ............. 299/15 |
| 4,121,499 | 10/1978 | Hay ............. 91/282 |
| 4,121,672 | 10/1978 | Tkach et al. ............. 175/19 |
| 4,651,833 | 3/1987 | Karpf et al. ............. 173/136 |
| 4,706,659 | 11/1987 | Matthews et al. ............. 128/92 VD |
| 4,840,237 | 6/1989 | Roemer ............. 175/19 |
| 4,886,128 | 12/1989 | Roemer ............. 175/19 |
| 4,909,419 | 3/1990 | Yamada et al. ............. 227/1 |
| 5,014,796 | 5/1991 | Gustafsson ............. 173/91 |
| 5,057,112 | 10/1991 | Sherman et al. ............. 606/79 |
| 5,108,400 | 4/1992 | Appel et al. ............. 606/79 |
| 5,152,352 | 10/1992 | Mandanis ............. 173/17 |
| 5,251,367 | 10/1993 | Ward et al. ............. 173/169 |

FOREIGN PATENT DOCUMENTS

| | | | |
|---|---|---|---|
| 0183874 | 6/1986 | European Pat. Off. ......... | B25D 9/14 |
| 3148708 | 7/1983 | Germany ............. | B25D 9/14 |

*Primary Examiner*—Scott A. Smith
*Attorney, Agent, or Firm*—Parmelee, Bollinger & Bramblett; George W. Rauchfuss, Jr.

[57] ABSTRACT

The impact tool is provided with a piston (15) oscillating within a cylinder (10). For selecting, with which piston impact surface the piston (15) impacts on the head (7) of a tool holder (2) and accordingly for the selection whether the impact tool generates forward or rearward strikes, respectively, the cylinder (10) is displaced pneumatically between two positions. The displacement occurs depending on the position of a switch (21). This changing of the impact direction is simple and makes it possible to fix the tool holder in the housing (1) making the impact tool sturdy.

10 Claims, 3 Drawing Sheets

PNEUMATIC IMPACT TOOL AND PISTON FOR A PNEUMATIC IMPACT TOOL

BACKGROUND OF THE INVENTION

The invention relates to a pneumatic impact tool or striking tool, respectively, particularly for surgical use. The tool has a housing, a cylinder/piston arrangement with a pneumatically driven oscillating piston, and a tool holder which is provided outside the housing with a tool adapter and which forms two impact faces for the piston inside the housing. The tool selectively generates strikes in forward direction or in rearward direction, respectively. The invention further relates to a piston for a pneumatic impact tool.

DESCRIPTION OF THE PRIOR ART

Pneumatic impact tools, particularly for surgical use, and for example for the driving of bone working tools (for example bone rasps) for working of the bearing surfaces of bones by the implantation of a prosthesis (for example a hip joint) are known from EP-A-452 543 and U.S. Pat. No. 5,152,352 and from WO 89/06516 and U.S. Pat. No. 5,108,400.

The impact tools shown in these documents are switched from one striking direction to the other by bringing the tool holder in different positions within the housing or by slidingly holding the tool holder in the housing. Holding and sealing the tool holder, which is subject to considerable lateral forces as well, is complicated. In the case of EP-A-452 543 reversal of the impact direction is caused by rotation of the tool holder held in the housing by threads, which is complicated. According to the WO 89/06516 on the other hand, reversal of the striking direction is provided only by pulling or pushing, respectively, on the housing, which causes a respective displacement of the tool holder relative to the housing. Such an impact tool, however, is not easy to operate since the reversal of the striking direction occurs not independently of holding and moving of the housing by the operator and can be triggered by accidental movements of the housing. Furthermore, with such a design the magnitude of the impacts changes with the displacement of the tool holder as well and therefore with the pulling or pushing force, respectively, which is exerted by the operator on the housing of the impact tool. This characteristic makes proper operation of such a tool a difficult task.

SUMMARY OF THE INVENTION

Hence it is a general object of the present invention to provide a pneumatic impact tool which does not have the mentioned disadvantages. It is therefore an object of the invention to provide an impact tool with reversible impact direction which can be reversed easily and in a well defined manner and without an influence on the impact direction by pulling or pushing forces, respectively, on the housing. Such forces shall moreover not influence the magnitude of the impacts, so as to render an impact tool that can be operated easily and predictably. It is a further object to provide an impact tool with a very sturdy design, particularly concerning the fixation of the tool holder in the housing, which is subject to considerable forces in different directions.

Now in order to implant these and still further objects of the invention, which will become more readily apparent as the description proceeds, the impact tool is manifested by the features that the tool holder is held by the housing in a essentially fixed position, that the cylinder is not provided by the housing itself but is a separate part arranged displaceable within the housing, and that manually operable switch means are provided for displacement of the cylinder, and that the pneumatically driven piston oscillating within the cylinder impacts on the first impact face or on the second impact face of the tool holder, respectively, depending on the position of the cylinder.

The active reversal of the striking direction by moving the cylinder from one position to another makes it on the one hand possible to use a nondisplaceable, sturdy tool holder which is easy to seal and makes it on the other hand possible to reverse impact directions independently of pulling and pushing forces acting on the housing.

EP-A-452 543 shows a stepped piston and the compressed air is controlled by the piston. To this end a connecting channel is provided in the housing, which has the disadvantage that the housing becomes complicated to manufacture. Furthermore, the impact tool has a larger outside diameter, making the handling of the tool more cumbersome to the surgeon. Still another object of the invention is therefore to provide a piston, preferably for use in the above outlined impact tool, that overcomes this disadvantage. This object is met by a piston for a pneumatic impact tool, in which the piston in a stepped piston oscillating controlled by compressed air in such a manner that compressed air acts permanently on an annular piston face and intermittently via a piston controlled connecting line on the piston head and that the connecting line is arranged within the piston and comprises a multitude of separate channels.

BRIEF DESCRIPTION OF THE DRAWING

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
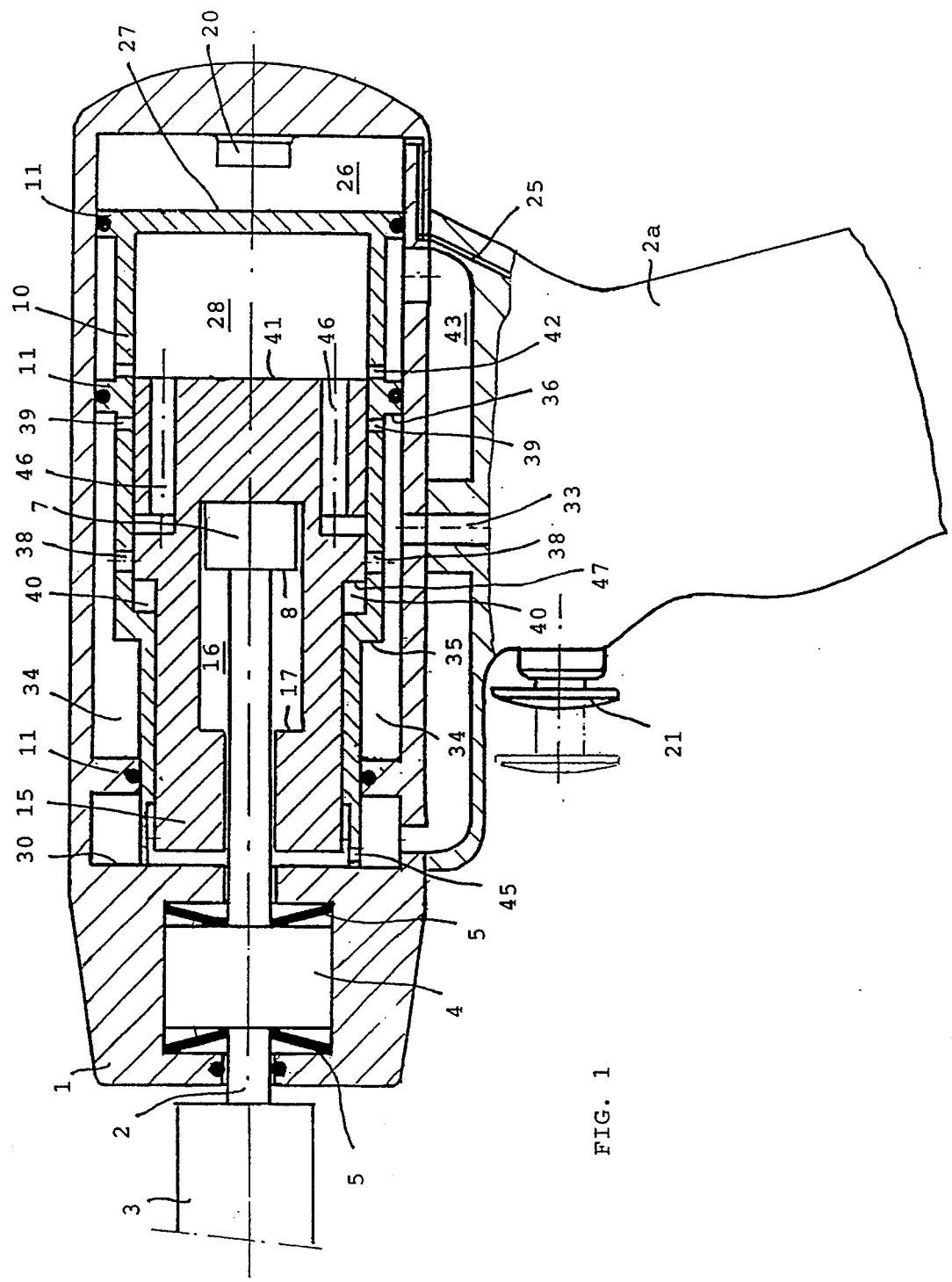
FIG. 1 is a fragmentary schematic sectional view of an impact tool according to the invention shown in the position for generating strikes in forward direction.

The impact tool shown as an example in the drawing comprises a housing 1 having a grip 2a which is only partly shown. A tool holder 2 is held by the housing. The tool holder 2 is provided at its front end with an adapter 3, shown only partly and in a general way, for the fixation of a tool for the working of bones, for example for a bone rasp. The tool holder 2 is held in the front part of the housing 1 by a block 4 which is arranged in a corresponding opening of the housing 1 and fixes the tool holder against lateral movements. For the fixation in longitudinal direction of the tool holder 2 there are preferably provided stiff plate springs 5 arranged between the block 4 and the housing which hold the tool holder 2 in an essentially fixed position. The plate springs serve a dynamic isolation or protection, respectively, of the housing against the strikes of the piston exerted on the tool holder. Such a protection of the housing can be attained as well by rubber elements or plastic elements, respectively, in the place of the plate springs 5. A completely rigid fixation of the tool holder within the housing can be used as well, since a displacement of the tool holder within the housing is not necessary for the function and the impact direction reversal. Inside of the housing 1 the tool holder 2 extends into a hollow space of the housing and is provided at its end with a head 7 having two impact faces 8 and 9, respectively (FIG. 2). A cylinder 10 is provided in the housing. This cylinder 10 is displaceable in longitudinal direction within the housing and is normally placed at one of the two end positions shown in FIG. 1 and FIG. 2, respectively. The cylinder 10 is guided by several guides 11 provided at the inner surface of the housing and the outer surface of the cylinder, respectively, where O-seals can be provided as well. A stepped piston 15 which is a hollow piston, is arranged within the cylinder. The hollow space 16 of the piston 15 encloses the head 7 of the tool holder and forms two impact surfaces 17 and 18, respectively. A stop 20 is provided at the rearward inner surface of the housing. A switch 21 for the control of the impact tool is provided outside of the housing. Further, there is a connection not shown in the drawing for connecting the impact tool to a suitable source of compressed gaseous fluid, e.g. air.

Figure 2:
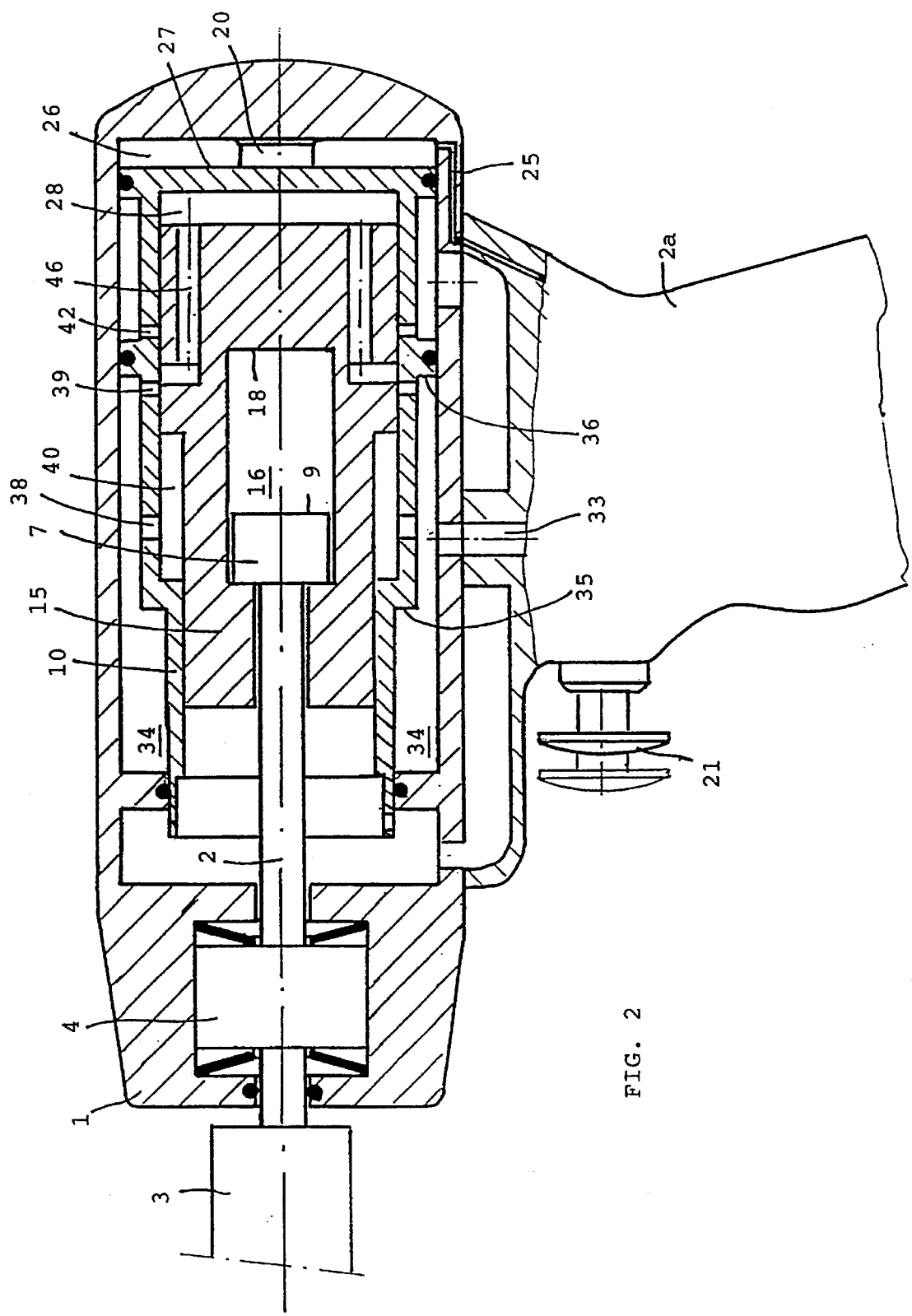
FIG. 2 is a similar fragmentary schematic view shown in the position for generating strikes in rearward direction.

The function of the impact tool shall be explained first with reference to FIG. 1 which shows the cylinder 10 in such a position that causes the impact tool to generate strikes on the bone working tool in forward direction.

To this end the operator of the impact tool brings the operating element or switch 21, respectively, into the right-hand position shown in bold lines in FIG. 1. This connects the compressed air channel 25 of the housing 1 with the compressed air connection of the impact tool and therefore with the compressed air source by a valve operated by the switch 21. This valve of a construction well known in the art is not shown in the drawing. The pressure of the compressed air source is for example 7 bar. Compressed air of this pressure consequently reaches now the chamber 26 via the channel 25. The chamber 26 is arranged in the rear part of the housing 1 and is limited by the inner walls of the housing and by the end plane 27 of the cylinder 10. The compressed air in chamber 26 exerts a force on the cylinder 10 which forces the cylinder 10 into the displaced position shown in FIG. 1, in which position the cylinder 10 is completely displaced towards the bone working tool and abuts with its front end on the inner wall 30 of the housing.

Compressed air is further brought by a channel 33 in the housing into a chamber 34 arranged between cylinder 10 and housing 1. This compressed air can be fed to the channel 33 by the valve mentioned before as well. But the compressed air can be fed to the channel by a separate valve as well. The compressed air in chamber 34 on the one hand exerts a force on the cylinder 10 by acting on its annular surfaces 35 and 36 which force is directed against the force exerted by the compressed air pressure on the end plane 27 of the cylinder 10 on the other hand. But since the area of the end plane 27 is larger than annular surfaces 35 and 36, the cylinder 10 is forced into the position shown in FIG. 1 nevertheless.

Openings 38 and 39 lead from the chamber 34 into the inner cylinder space. By these openings 38 and 39 the compressed air necessary for the oscillating movement of the piston is brought into the cylinder.

The movement of the piston itself is attained in generally the same way as known from EP-A-452 543. In the left dead center position of the piston 15 shown in FIG. 1 the piston acts by its impact face 18 on the impact surface 9 of the head 7 of the tool holder 2 to generate a forward strike on the bone working tool. The piston will be accelerated from this shown left dead center position to the right by expansion of the air that has been compressed in the chamber 40 which is limited by the step of the piston 15 and by a stage of the cylinder 10. During the movement of the piston 15 to the right the piston opens the opening 38 from the chamber 34 to the inner space of the cylinder. Accordingly, compressed air enters into the chamber 40 which is getting larger by the right-hand movement of the piston. The chamber 28 limited by the front end 41 of the piston and the inside walls of the cylinder 10 is at the position of the piston shown in FIG. 1 without overpressure, that is on a pressure level corresponding to ambient atmospheric pressure. This is the case since the chamber 28 is at the shown piston position still connected to ambient pressure by outlets 42 situated in the cylinder wall and by the chamber 43 in the housing which is open to ambient pressure by openings in the housing not shown in the drawing. During the rightward piston movement the piston 15 closed the openings 42 and the air trapped in the chamber 28 that is getting smaller by piston movement is compressed. But by the mentioned supply of compressed air into chamber 40 via the opening 38 there is still an acceleration of the piston in the right direction. As soon as the piston 15 attains on its way to the right-hand dead center position such a position that the openings 39 from the chamber 34 into the cylinder connect with the radially extending part of the channels 46 within the piston 15 compressed air is supplied via openings 39 and channels 46 into the chamber 28 as well. By this feeding of compressed air into chamber 28 a smooth braking of the piston 15 is attained which piston thus reaches its right dead-center position and is then accelerated by the compressed air in left-hand direction towards the tool holder. Expansion in chamber 28 accelerates the piston until the piston itself opens the outlets 42 and therefore connecting chamber 28 to ambient pressure again. During its movement in left-hand direction the piston again impacts with its impact face 18 on the impact surface 9 of the head 7, generating a forward strike, and attains again the position shown in FIG. 1 from where the piston again and as described above will move in right hand direction and will be gently braked (without hitting the head 7) as explained at its right-hand dead center position. Thus, when the cylinder 10 is in this position as shown in FIG. 1 the impact tool generates forward strikes only. Openings 45 are arranged in the front cylinder walls, whereby the frontal chamber is always connected via outlets in the housing to ambient pressure so that the piston is not braked by compression in this chamber.

FIG. 2 shows the same impact tool in a position wherein only rearward strikes are generated on the bone working tool. The same reference numerals are used for the same elements as in FIG. 1. In FIG. 2 the operating means or switch 21, respectively, is depressed by the operator less far than in FIG. 1 and the switch is in a middle position as indicated by bold lines compared to its rest position indicated by faint lines. In this case the channel 25 in the housing 1 is not connected by the valve to the compressed air source but to ambient pressure. Consequently, the chamber 26 is at ambient pressure as well. Via channel 33 in the housing 1 compressed air is still fed in this switch position as well to the chamber 34, and accordingly by the pressure of the compressed air on the outside annular surfaces 35 and 36 of the cylinder 10 the cylinder is moved into its right hand end position shown in FIG. 2 wherein the end plane 27 of the cylinder 10 abuts on the stop 20. By this displacement of the cylinder 10 within the housing it occurs that the piston 15, which has been displaced together with the cylinder relative to the tool holder 2 which is fixed in the housing, impacts now with its impact face 17 on the impact surface 8 of the head 7. But the piston 15 now impacts no longer on its way to the left with its impact face 18 on the impact surface 9 of the head 7 but is gently braked by the air trapped and compressed in chamber 40. In all other respects the oscillating movement is caused as described in connection with FIG. 1 and is therefore not repeated again. The oscillating piston therefore generates only rearward strikes of the impact tool when the switch 21 and consequently the cylinder 10 is in its position shown in FIG. 2.

In a third position of the operating means 21, which is depicted as leftmost position by faint lines, furthermore the supply of compressed air via channel 33 into chamber 34 is ended. In this case the piston 15 is no longer driven and the impact tool does not generate strikes at all. Consequently the operation of the impact tool shown is as follows: With the switch 21 at its rest position the impact tool is deactivated. When the switch is about halfway pushed in to the right, the tool generates rearward strikes only (FIG. 2). When the switch is further pushed in to its rightmost direction by the operator the impact tool generates forward strikes only (FIG. 1).

The shown pneumatic displacement of the cylinder 10 is to be understood by way of example only. Of course a displacement by a lever to be operated by hand and mechanically coupled to the cylinder or another way of displacing the cylinder is possible as well.

Figure 3A:
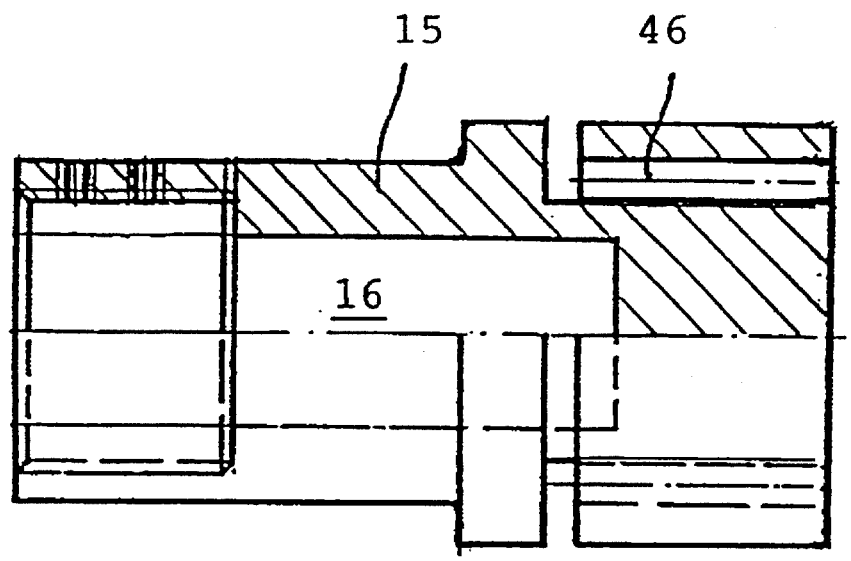
FIG. 3A is a partly sectional side elevation and FIG. 3B a front view of a piston for an impact tool.
Figure 3B:
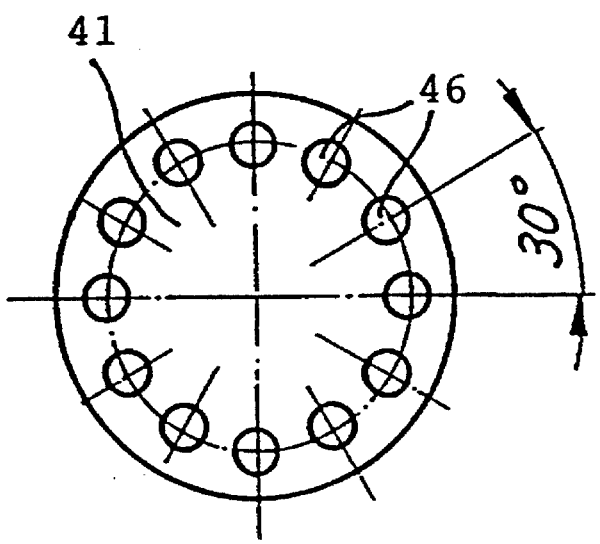

FIGS. 3A and 3B shows a partly sectional view of the piston according to the invention. This piston can be used by an impact tool according to the FIG. 1 and 2 as has been shown therein. But this piston can be used with an impact tool as shown for example by EP-A-452 543. The piston according to the invention is provided by a plurality of control channels 46. By this feature a control channel within the housing can be omitted, whereby the manufacture of the housing can be simplified and the tool can be more compact. Moreover, by a larger number of channels, the impact energy can be increased, since more compressed air can be fed via the multitude of channels.

Preferably the impact tool is designed according to the rules known from EP-A-452 543 whereby the relation between the forward momentum and the rearward momentum generated on the bone working tool is 1. Accordingly a first parameter A is defined as follows $$A = \frac{A_1 P_0}{A_2 P_2}$$

wherein $A_1$=size of the end plane 41 of the piston $A_2$=size of the annular surface 47 of the piston $P_0$=value of the ambient pressure (approx. 1 bar)

$P_2$=value of the pressure of the compressed air source (approx. 7 bar)

Two further parameters are defined as follows:

$$V_u = \frac{V_{12}}{V_A} \text{ and } V_o = \frac{V_T}{V_A}$$

wherein $V_A$ is the volume of the control channels (including the volume of the annular groove) plus the volume of the upper cylinder chamber 28 at the piston position where the control channels are just being opened and $V_T$ is the volume of the control channels 46 (including the groove) plus the volume of the upper cylinder chamber at the upper (right-hand) piston dead-center position.

The momentum relation of 1 is attained when the parameter are within the following ranges $$0.1 \leq A \leq 0.5$$

$$0 \leq V_o \leq V_u \leq 1$$

Preferably the parameters $V_o$ and $V_u$ are in the range of 0.1 to 0.8.

While there are shown and described present preferred embodiments of the invention, it is to be distinctly understood that the invention is not limited thereto, but may be otherwise variously embodied and practiced within the scope of the following claims.

I claim:

1. A pneumatic impact tool, particularly for surgical use, comprising:

a housing;

a tool holder held by said housing and having a first section inside said housing and a second section outside of said housing, said first section being provided at a free end thereof with a head having a first and a second impact surface, and said second section being provided at a free end thereof with a working tool holding means;

a cylinder provided within said housing;

a piston provided within said cylinder and having an inner hollow space enclosing said head, said piston being driveable by pneumatic pressure to oscillate within said cylinder, and a manually operable switch means provided for selectively slidably displacing said cylinder within said housing and relative to said head from a first position to a second position, and wherein in said first position of said cylinder said oscillating piston impacts only on said first impact surface of said head and in said second position of said cylinder said oscillating piston impacts only on said second impact surface of said head.

2. Pneumatic impact tool according to claim 1, wherein said cylinder is displaced by pneumatic pressure.

3. Pneumatic impact tool according to claim 1, wherein said switch means comprise a valve, which supplies in one switch position thereof compressed air to at least one annular surface of an outer wall of said cylinder and in another switch position supplies compressed air to an end plane of the outer cylinder.

4. Pneumatic impact tool according to claim 3, wherein said at least one annular surface of said outer cylinder wall is part of a wall of said first chamber arranged between said housing and said cylinder outer wall.

5. Pneumatic impact tool according to claim 1, wherein a first chamber continuously fed with compressed air is provided between said housing and the cylinder outer wall, from which chamber at least two openings lead into an interior of the cylinder, said at least two openings being arranged at a distance from each other in a longitudinal direction of said cylinder.

6. Pneumatic impact tool according to claim 5, wherein said piston is a stepped piston which oscillates controlled by compressed air acting continuously on an annular piston surface and acting only intermittently on a planar end surface of said piston, and wherein said annular piston surface is acted upon by compressed air from said first chamber via one of said at least two openings.

7. Pneumatic impact tool according to claim 6, wherein said planar end surface of said piston is acted upon intermittently by compressed air via a piston controlled control line.

8. Pneumatic impact tool according to claim 7, wherein said control line is provided by a plurality of channels in said piston, said channels are intermittently connected with said chamber depending on movement of the piston via a second opening of said at least two openings.

9. Pneumatic impact tool according to claim 5, wherein said at least one annular surface of said outer cylinder wall is part of a wall of said first chamber arranged between said housing and said cylinder outer wall.

10. Pneumatic impact tool according to claim 1, wherein said tool holder is fixedly mounted in said housing against lateral forces by a block-shaped bearing means, and wherein fixation of said tool holder in a longitudinal direction is provided by springs or elastic rubber elements or elastic plastic elements, which are inserted between said block-shaped bearing means and said housing.

* * * * *